(12) United States Patent
Barker

(10) Patent No.: US 11,033,595 B2
(45) Date of Patent: Jun. 15, 2021

(54) PLANT BASED EMOLLIENT

(71) Applicant: Wynn Edison Barker, Lehi, UT (US)

(72) Inventor: Wynn Edison Barker, Lehi, UT (US)

( * ) Notice: Subject to any disclaimer, the term of this patent is extended or adjusted under 35 U.S.C. 154(b) by 0 days.

(21) Appl. No.: 16/510,770

(22) Filed: Jul. 12, 2019

(65) Prior Publication Data

US 2020/0016226 A1    Jan. 16, 2020

Related U.S. Application Data

(60) Provisional application No. 62/697,024, filed on Jul. 12, 2018.

(51) Int. Cl.
| | | |
|---|---|---|
| *A61K 36/00* | (2006.01) | |
| *A61K 36/886* | (2006.01) | |
| *A61K 9/00* | (2006.01) | |
| *A61K 36/889* | (2006.01) | |
| *A61K 47/14* | (2017.01) | |
| *A61K 47/44* | (2017.01) | |
| *A61K 9/107* | (2006.01) | |
| *A61K 47/02* | (2006.01) | |

(52) U.S. Cl.
CPC .......... *A61K 36/886* (2013.01); *A61K 9/0014* (2013.01); *A61K 9/107* (2013.01); *A61K 36/889* (2013.01); *A61K 47/02* (2013.01); *A61K 47/14* (2013.01); *A61K 47/44* (2013.01)

(58) Field of Classification Search
None
See application file for complete search history.

(56) References Cited

FOREIGN PATENT DOCUMENTS

CN    102274380 A    * 12/2011

* cited by examiner

*Primary Examiner* — Qiuwen Mi
(74) *Attorney, Agent, or Firm* — Terrence J. Edwards; TechLaw Ventures, PLLC

(57) ABSTRACT

The disclosure relates to a plant based emollient composition. The composition includes palm kernel oil and an aloe vera plant extract. The composition is useful alone or as a vehicle for small quantities of herbs, vitamins, medications, minerals, vinegars, essential oils (as examples) added during the composition's liquid phase.

12 Claims, 3 Drawing Sheets

Administering A Composition To A User, Wherein The Composition Includes:
Palm Kernel Oil; And
Aloe Vera Plant Extract;
Wherein The Palm Kernel Oil Comprises From About 40% To About 60% By Weight Of The Total Composition.

102

PLANT BASED EMOLLIENT

CROSS REFERENCE TO RELATED APPLICATIONS

This application claims the benefit of U.S. Provisional Application No. 62/697,024, filed Jul. 12, 2018, which is incorporated herein by reference in its entirety, including but not limited to those portions that specifically appear hereinafter, the incorporation by reference being made with the following exception: In the event that any portion of the above-referenced provisional application is inconsistent with this application, this application supersedes said above-referenced provisional application.

TECHNICAL FIELD

The disclosure relates generally to a plant based emollient, and more specifically, to a composition of aloe vera and palm kernel oil to create an emulsion.

BACKGROUND

Plant based products can provide a healthy and nontoxic alternative to synthetic and manufactured products for a variety of applications. Some applications where plant based products may be particularly desirable include skin and health products, cleaning products, and medical treatments. Plant based products can eliminate many of the toxins and dangers associated with toxic manufactured products, particularly when used around children or animals. However, in some applications, plant based products do not provide the same benefits or effectiveness of synthetic products.

For example, there exist many products available for skin-based issues or health conditions. Consumers of skin products have numerous options when selecting lotions or creams for softening and/or moisturizing skin or selecting products for reducing skin irritation. Further, in the context of treating skin burns, such as a sunburn, there exist many synthetic products that can provide relief to a user or even promote skin healing after a burn. However, these synthetic products often include numerous toxic chemical or are produced in factories with toxic chemicals. Such products are not safe to consume and can be dangerous for children or animals. Additionally, the toxic and synthetic materials in these products can include carcinogens that harm the body or may cause unknown damage to the body when used over a long time period.

Therefore, it is desirable to produce compositions with natural ingredients that are safe if consumed and do not cause irritation to sensitive skin. Disclosed herein are compositions formed entirely of safe and nontoxic natural products that provides unexpectedly good results for treating skin issues or conditions including skin burns and dry sin, and for softening and improving a user's skin.

DETAILED DESCRIPTION

Figure 1:
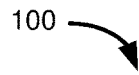
FIG. 1 is a schematic diagram of a method for treating a skin condition in a user.

Numerous products exist in the marketplace that can be effective for treating skin issues and skin conditions such as burns or rashes, or for softening and improving skin. However, such products typically include many toxic chemicals and cannot safely be stored in reach of children or animals. Such products can be poisonous and even deadly if consumed and cause significant skin irritation.

Disclosed herein are compositions comprising only natural, safe, and nontoxic components. Such compositions as disclosed herein provide effective and unexpectedly good relief for skin burns, including at least first and second degree burns. Additionally, such compositions as disclosed herein provide relief for skin irritations, skin calluses, and dry or tough skin. Further, compositions disclosed herein provide an effective cleaning substance for cleaning skin and other surfaces.

Compositions prepared according to the methods disclosed herein provide unexpectedly good results for maintaining a natural plant based product that does not include harmful chemicals or toxic additives. Most skin emollients known in the art, including lotions, salves, creams, and so forth, include numerous harmful chemicals that are added for the purpose of maintaining a solid or thick substance having a consistent texture or viscosity. The compositions disclosed herein comprise only natural ingredients that could be ingested without causing harm to a user. Additionally, the compositions disclosed herein comprise only necessary ingredients that provide health benefits, cleaning benefits, or other benefits that are not specifically directed to maintaining a certain viscosity or solid state.

The compositions disclosed herein may include palm kernel oil that is extracted by one or more methods of palm kernel oil extraction. Palm kernel oil is regarded as a safe and healthy substance that can provide numerous health benefits. However, palm kernel oil has a relatively low melting point and will not stay in a solid form without being chilled or processed. Disclosed herein are methods and processes for preparing a composition including palm kernel oil that may be maintained at a solid state without the addition of harmful chemicals or toxic additives.

Further, the compositions disclosed herein may include aloe vera plant extract. Similar to palm kernel oil, aloe vera is also regarded as a healthy substance that can provide health benefits to a user without the harmful side effects of toxic synthetic substances. However, aloe vera plant extract is a liquid at room temperature or at common refrigeration temperatures. Therefore, it is difficult to apply aloe vera plant extract to skin or other substances as an emollient or skin salve. Disclosed herein are methods and processes for preparing a composition including aloe vera plant extract that may be maintained at a solid state without the addition of harmful chemicals or toxic additives.

The compositions and methods disclosed herein provide unexpectedly good results for preparing a healthy and consumable emollient without the addition of additives that do not serve to provide any additional health benefits to a user. The methods disclosed herein provide for a composition that includes aloe vera plant extract and palm kernel oil and may still be maintained in a viscous and spreadable form that is suitable for use as a skin salve. The methods and compositions disclosed herein provide unexpectedly good results for preparing a user-friendly skin emollient that is effective for treating skin conditions such as sunburns and excessive dryness.

In an embodiment, a composition includes palm kernel oil and aloe vera plant extract. The palm kernel oil and the aloe vera plant extract may be present in a 1:1 or nearly a 1:1 ratio. The composition may serve as an effective carrier of numerous other components, including essential oils, herbs, vinegars, vitamins, and more. In an embodiment, the composition may include palm kernel oil from about 40% to about 60% by weight the total composition and may further include the aloe vera plant extract from about 40% to about 60% by weight the total composition. The composition may be stable in a solid state at a temperature below at least 25° Celsius. The composition may be applied topically for treating skin burns, reducing skin irritation, softening skin, and reducing skin calluses. The composition may further be used for effectively cleaning skin and other surfaces.

In an embodiment, the composition is safe for human or animal consumption and may be made of only food-grade and safe ingredients. In another embodiment, the composition may be made of non-food grade ingredients.

In an embodiment, a plant based composition comprising liquid palm kernel oil and liquid aloe vera juice is formulated such that the composition is stable in a solid state at a temperature below at least 25° Celsius. The liquid palm kernel oil and the liquid aloe vera juice may be combined in a 1:1 or nearly 1:1 ratio and may further be combined with other additives such as essential oils, vinegars, vitamins, herbs, and so forth. The composition may be warmed such that all components can be thoroughly mixed. The composition may be chilled in a refrigerated environment and/or cooled at room temperature until at least a portion of the composition has transitioned to a solid state. The composition may be agitated to increase viscosity of the composition. In an embodiment, the composition is agitated in a refrigerated environment to hasten solidification of the composition as the agitation ensures that the multiple components, including the palm kernel oil and the aloe vera juice, are thoroughly and consistently incorporated. The composition may be agitated in a sealed container such that the composition remains sealed in the sealed container until it is ready to be used for one or more useful applications.

In describing and claiming the subject matter of the disclosure, the following terminology will be used in accordance with the definitions set out below.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element, step, or ingredient not specified in the claim.

As used herein, "effective amount" means an amount of an ingredient or a component of the product that is nontoxic, but sufficient to provide the desired effect and performance at a reasonable benefit/risk ratio attending any dietary supplement or product. For example, an effective amount of a vitamin or mineral is an amount sufficient to prevent a deficiency thereof and to reduce the incidence of some adverse effects.

Unless defined otherwise, all technical and scientific terms used herein have the same meanings as commonly understood by one of ordinary skill in the art to which this disclosure pertains and belongs.

Further, although specific implementations of the disclosure have been described, the disclosure is not to be limited to the specific forms or arrangements of parts so described. The scope of the disclosure is to be defined by the claims appended hereto, if any, any future claims submitted here and in different applications, and their equivalents.

Compositions as disclosed herein provide numerous benefits having unexpectedly good results across multiple applications, including health and wellness applications along with cleaning applications. For example, compositions as disclosed herein may be used for cleaning various substances, including skin and other surfaces. The specialized composition of aloe vera and palm kernel oil as disclosed herein generates a compound with unique capabilities to lift dirt, grime, makeup, oil, and other components out of various material and/or surfaces. The specialized composition disclosed herein provides an unexpectedly good result in removing makeup from skin while also serving as an effective emollient of the skin to smooth and soften the skin without irritating the skin or causing undue discomfort for the user.

Further for example, compositions as disclosed herein provide unexpectedly good results for the treatment of skin burns, including at least first degree and second degree burns. The compositions of the present disclosure provide soothing qualities to reduce pain caused by skin burns. Additionally, compositions as disclosed herein enable the release of heat trapped in skin layers due to burn in the skin. The release of heat enables the user to feel quick relief from the pain associated with the burn. Additionally, the release of heat halts the progression of further damage done to skin cells and other tissues in the body. When the progression of damage is halted due to the application of compositions as disclosed in the present application, the body is able to heal at a quicker rate.

An embodiment of the composition disclosed herein includes aloe vera plant extract. The aloe vera plant extract may be derived from an inner fillet of the plan or from the full leaf of the plan. When the aloe vera plant extract is derived from the inner filet of the aloe vera plant, the extract may provide numerous health benefits, including promoting optimal digestive health in a user and providing support for optimal immune system health in the user. Additionally, aloe vera plant extract from the inner fillet may increase a user's ability to absorb nutrients from food and reduce levels of free radicals in the body. When the aloe vera plant extract is derived from a whole leave of the aloe vera plant, the aloe vera extract may provide external or topical soothing properties for a user, including relief for skin irritations or skin burns.

An embodiment of the composition disclosed herein includes palm kernel oil. Palm kernel oil is an edible extract from the kernel of the oil palm *Elaeis guineensis*. Palm kernel oil has a high saturated fat content and may have a total fat concentration up to 99 wt % with a saturated fat concentration up to 82 wt %. The saturated fat in palm kernel oil includes lauric acid, and in some embodiments the palm kernel oil may include up to 47.8 wt % lauric acid. Other significant saturated fats in palm kernel oil include myristic acid, palmitic acid, and caprylic acid. Palm kernel oil further includes monounsaturated fats and may include monounsaturated fats in a concentration of about 15 wt %. Palm kernel oil further includes polyunsaturated fats in a concentration of about 2 wt %.

The composition disclosed herein may use palm kernel oil produced by one or more different methods. Palm kernel oil can be produced by a mechanical process, a solvent process, or a traditional process. Before the palm kernel oil can be extracted the kernel must be removed from the palm itself. This is accomplished by separating the nuts from the fiber and having the nuts then left to dry. Later the kernels are separated from the shells using a combination of winnowing and hydrocyclones. For the mechanical process of extracting the palm kernel oil, the palm kernel goes through a series of steps to prepare the kernel to be pressed. To begin, the kernel is cleaned and then option steps include reducing the size of the kernel, flaking and steam conditioning. Once this has been accomplished the kernel is ready to be screw pressed. During the press process some oil is clean and can be sent to storage, the remaining portion of the oil contain 'fines and foots' which need to be removed. The 'dirty' oil is sent to a filter where the impurities are removed and the 'clean' oil is sent to storage and joins the oil sent from the press stage. The solvent process for extracting the oil from palm kernels shelling the palm nuts, cleaning the kernel and processing the kernel into flakes. Hexane and other solvents are used to wash the palm kernel oil from the prepared flakes. The solvents must be removed from the oil and flakes after the oil has been washed out of the flakes. This is accomplished by heating/steaming the flakes and a distillation system is used for the oil. Crude palm oil or palm kernel oil must be further processed to make an edible product. Edible palm oil is refined to improve the flavor, odor, color and stability using processes that degum, bleach, deacidify and deodorize the oil. These processes remove contaminants such as phosphatides, free fatty acids and pro-oxidants. The traditional process begins with the shelling of palm nuts. The shells then need to be separated from the kernels which is typically performed in a clay bath, a mixture of clay and water. The density of the clay bath causes the shells to sink and the kernels to float. The floating kernels are removed from the bath and cleaned and dried. The dry kernels are then heated or fried in old oil and then pounded or ground into a paste. The paste is mixed with a small quantity of water and heated to allow for the release of the palm kernel oil which is skimmed from the top.

In an exemplary embodiment, the composition is generated with unrefined palm kernel oil that has not been refined, bleached, and/or deodorized. Additionally, the unrefined palm kernel oil is not hydrogenated or fractionated.

In an embodiment, the composition includes one or more vinegars. Vinegars suitable for use in the present composition include, for example, white vinegar, apple cider vinegar, wine vinegar, rice vinegar, malt vinegar, cane vinegar, and coconut vinegar. The one or more vinegars may provide certain health or cleaning benefits in various applications of the composition. The specialized mixture of palm kernel oil and aloe vera as disclosed herein, along with the specialized methods for generating the disclosed composition, provide an unexpectedly good means for holding the one or more vinegars consistently throughout the composition.

In an embodiment, the composition includes one or more essential oils. The one or more essential oils may be selected for certain health properties that may be applicable to different uses or consumptions of the composition. Additionally, the one or more essential oils may be selected for a scent or aroma that is pleasant to a user and may counteract a smell of other ingredients in the composition, including one or more vinegars added to the composition.

In an embodiment, the composition is mixed and/or agitated in a refrigerated environment. In an embodiment, the composition, including the palm kernel oil and the aloe vera, are mixed and placed on a cold surface in a refrigerated environment. The temperature of the composition is monitored over time. As the composition cools and the temperature of the composition nears 16° Celsius, the composition will begin to transition to a solid state near the cold surface of the refrigerated environment. The composition is agitated at about 16° Celsius when the composition begins to transition to the solid state. The composition is agitated for about 30 seconds to about 90 seconds and then the agitated is slowed and discontinued. The composition is left undisturbed such that the composition can set and transition fully to the solid state.

In an embodiment, the composition is agitated with a pneumatic paint shaker or other agitation device to provide vigorous and prolonged shaking as the composition is cooling and beginning to transition to the solid state. In an embodiment, the composition is agitated in a refrigerated environment and/or agitated near cool air generated by an air conditioning device or other suitable device. In an embodiment, the composition is agitated in an environment between about −3.0° Celsius to about 5.0° Celsius.

In an embodiment, the composition is cooled in a refrigerated environment and the composition is agitated before any portions of the composition begin to solidify. The composition may be continually agitated in the refrigerated environment (may be refrigerated by the presence of, for example, an air conditioning unit or a refrigeration unit) until the composition begins to solidify. The composition then rests in the refrigerated environment such that the composition fully transitions to the solid state undisturbed and unagitated.

In an embodiment, the composition includes liquid palm kernel oil and liquid aloe vera juice along with one or more additional components such as sodium benzoate, phosphoric acid, one or more preservatives, one or more essential oils, and/or one or more vinegars. The composition may be warmed until all components are evenly distributed. The composition may be cooled in a refrigerated environment or at room temperature. In an embodiment, the composition is agitated throughout warming and throughout the cooling process.

The methods for producing a palm kernel oil and aloe vera composition as disclosed herein provide unexpectedly good results. The resulting composition is fully mixed and provides a smooth consistency suitable for topical applications for a human user. The consistency of the composition when generated by the methods disclosed herein provides a nearly one-to-one ratio of palm kernel oil and aloe vera in all portions of the composition. This ratio provides a composition having a suitable viscosity for topical application and provides significant health benefits for a user. The health benefits provided by the disclosed composition enhance and increase the benefits received by either of palm kernel oil or aloe vera when used alone.

The composition disclosed herein provides a superior carrier for vitamins and minerals to be topically applied and/or ingested by a user. The disclosed ratio of palm kernel oil and aloe vera, when prepared by the methods disclosed herein, provides an unexpectedly effective carrier for micronutrients, vitamins, minerals, herbs, vinegars, and essential oils. The viscosity of the composition when prepared by the disclosed methods enables additives to be included consistently throughout the composition, and therefore topically applied consistently and/or ingested consistently.

Now turning to the figures, FIG. 1 is a schematic block diagram of a method 100 for treating a skin condition and/or treating a skin irritation and/or softening skin in a user. The method 100 includes administering at 102 a composition to the user. The composition includes palm kernel oil and aloe vera plant extract. The composition is such that the palm kernel oil comprises from about 40% to about 60% by weight of the total composition.

Figure 2:
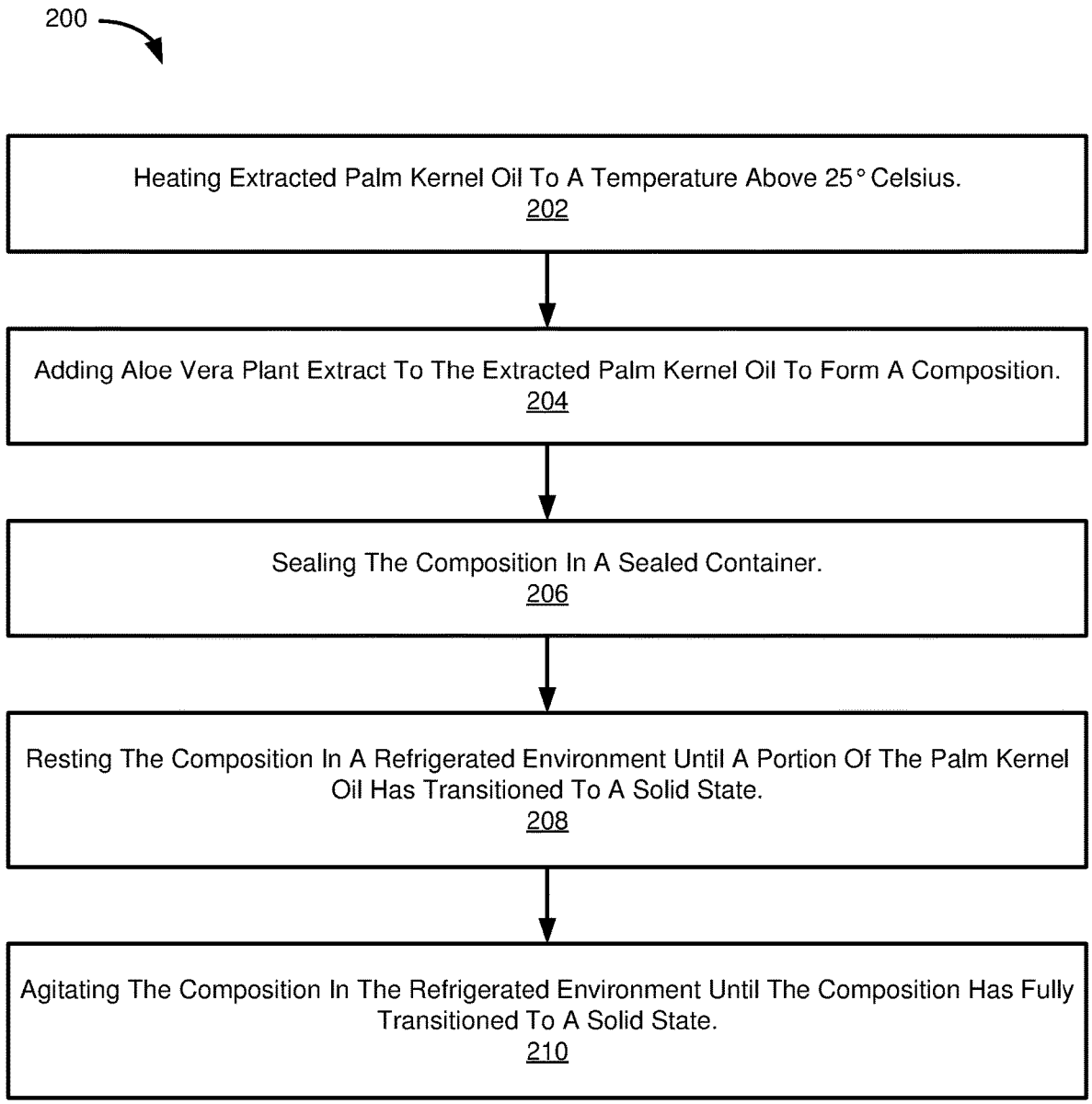
FIG. 2 is a schematic flow chart diagram of a method for preparing a plant based emollient.

FIG. 2 is a schematic block diagram of a method 200 for making a composition. The method 200 begins and palm kernel oil is heated to a temperature above 25° Celsius at 202. Aloe vera plant extract is added to the palm kernel oil to form a composition at 204. The composition is sealed in a sealed container at 206. The composition rests in a refrigerated environment until a portion of the palm kernel oil has transition to a solid state at 208. The composition is agitated in the refrigerated environment until the composition has fully transitioned to a solid state at 210.

Figure 3:
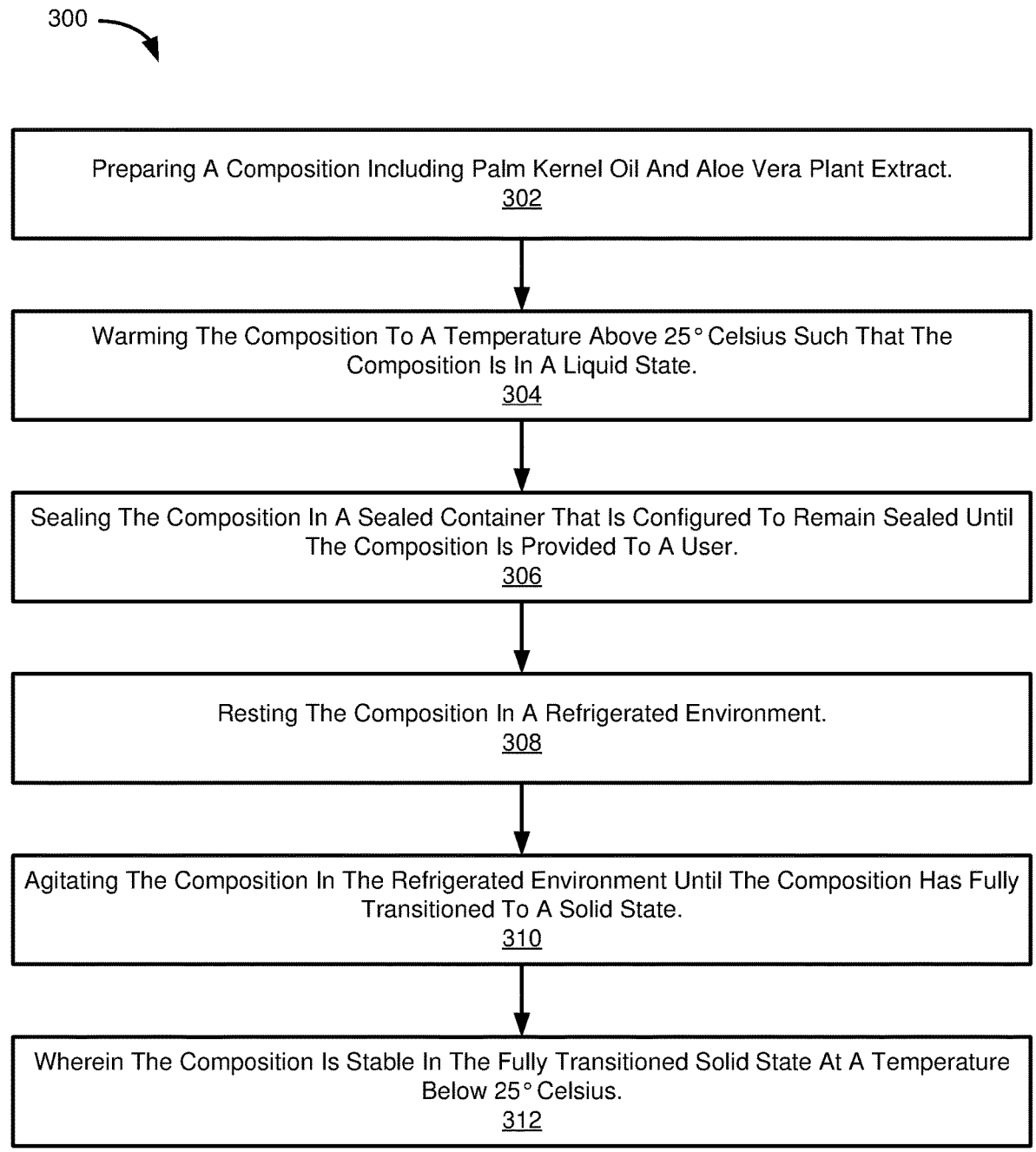
FIG. 3 is a schematic flow chart diagram of a method for preparing a plant based emollient.

FIG. 3 is a schematic block diagram of a method 300 for making a composition. The method 300 begins and a composition is prepared at 302, wherein the composition includes palm kernel oil and aloe vera plant extract. The composition is warmed at 304 to a temperature above 25° Celsius such that the composition is in a liquid state. The composition is sealed at 306 in a sealed at 306 container that is configured to remain sealed until the composition is provided to a user for use. The composition rests at 308 in a refrigerated environment. The composition is agitated at 310 in the refrigerated environment until the composition has fully transitioned to a solid state. The method 300 is such that the composition is stable in the fully transitioned solid state at a temperature below at least 25° Celsius (see 312).

Examples

Chart 1 below shows an example embodiment of the composition. In the example embodiment, the components are mixed in a sealable container. The sealable container has a sufficient volume compared with a total volume of the composition such that there is room for the composition to be agitated within the sealable container. In an embodiment, the sealable container has a volume of about one to two times larger than a total volume of the composition. In an embodiment, the sealable container is a container intended for retail distribution and/or sale such that the composition is never opened or exposed to environmental elements after agitation or before sale or transfer to a user. In the exemplary embodiment illustrated in chart 1, the composition is mixed at a temperature above 24° Celsius. The aloe vera plant extract may be derived from the inner fillet of the plan or from the entire leaf.

CHART 1

| Component | Weight Percent Total Composition |
|---|---|
| Palm kernel oil | 50.00 |
| *Aloe Vera* plant extract | 49.00 |
| Phosphoric acid | 1.00 |
| Sodium benzoate | 0.05 |

Example 1 is a composition. The composition includes palm kernel oil and an aloe vera plant extract. In the composition, the palm kernel oil is present in an amount from about 40% to about 60% by weight of the total composition.

Example 2 is a composition as in Example 1, wherein the aloe vera pant extract comprises from about 40% to about 60% by weight of the total composition.

Example 3 is a composition as in any of Examples 1-2, wherein the palm kernel oil and the aloe vera plant extract are present in a 1:1 ratio.

Example 4 is a composition as in any of Examples 1-3, wherein the aloe vera plant extract comprises one or more of: aloe vera plant extract from an inner fillet of an aloe vera plant; or aloe vera plant extract from a whole leaf of an aloe vera plant.

Example 5 is a composition as in any of Examples 1-4, wherein the palm kernel oil is extracted by way of one or more of: a mechanical process; or a wet process using solvents. The composition is such that the palm kernel oil is not refined, bleached, or deodorized.

Example 6 is a composition as in any of Examples 1-5, wherein the palm kernel oil is partially hydrogenated.

Example 7 is a composition as in any of Examples 1-6, wherein the palm kernel oil is fractionated to isolate one or more of lauric acid, caprylic acid, or capric acid.

Example 8 is a composition as in any of Examples 1-7, wherein the palm kernel oil and the aloe vera plant extract are agitated in a sealed container that remains sealed until opened for consumption.

Example 9 is a composition as in any of Examples 1-8, further comprising one or more of an essential oil or a vinegar.

Example 10 is a composition as in any of Examples 1-9, further comprising one or more of phosphoric acid or sodium benzoate.

Example 11 is a composition as in any of Examples 1-10, further comprising an effective amount of one or more preservatives.

Example 12 is a composition as in any of Examples 1-11, wherein the composition is prepared for topical application.

Example 13 is a method of treating a skin condition in a user. The method includes administering a composition to the user, wherein the composition includes palm kernel oil and aloe vera plant extract. The composition is such that the palm kernel oil comprises from about 40% to about 60% by weight of the total composition.

Example 14 is a method as in Example 13, wherein the aloe vera plant extract comprises from about 40% to about 60% by weight of the total composition and wherein the palm kernel oil and the aloe vera plant extract are present in about a 1:1 ratio.

Example 15 is a method as in any of Examples 13-14, wherein the aloe vera plant extract comprises one or more of: aloe vera plant extract from an inner fillet of an aloe vera plant; or aloe vera plant extract from a whole leaf of an aloe vera plant.

Example 16 is a method as in any of Examples 13-15, wherein the palm kernel oil is extracted by way of one or more of: a mechanical process; or a wet process using solvents. The composition is such that the palm kernel oil is not refined, bleached, or deodorized.

Example 17 is a method as in any of Examples 13-16, wherein the palm kernel oil and the aloe vera plant extract are agitated in a sealed container and wherein the sealed contained remains unopened until providing the composition to the user.

Example 18 is a method as in any of Examples 13-17, wherein preparation of the composition comprises: sealing the composition in a sealed container when the palm kernel oil and the aloe vera plant extract are in liquid form; resting the composition in the sealed container in a refrigerated environment until a portion of the palm kernel oil transitions to a solid form; and agitating the composition in the sealed container until the composition transitions to a solid form.

Example 19 is a method as in any of Examples 13-18, wherein the composition further comprises one or more of an essential oil or a vinegar, wherein the vinegar comprises one or more of white vinegar, apple cider vinegar, malt vinegar, wine vinegar, or coconut vinegar.

Example 20 is a method as in any of Examples 13-19, wherein the composition is provided to the user for topical application on a skin burn site of the user.

Example 21 includes the composition as in any of Examples 1-20, wherein the composition is agitated at a temperature above 25° Celsius and creates an emulsion that, when cooled while agitated, is reduced relative to the increasing viscosity of the composition, will form a white plant based emollient that is stable below 25° Celsius.

Example 22 includes the composition as in any of Examples 1-21, wherein the composition is stable in a solid form at a temperature below 25° Celsius.

Example 23 includes the composition as in any of Examples 1-22, wherein the composition is used alone, or as a vehicle for small quantities of herbs, vitamins, medications, minerals, vinegars, essential oils that are added to the composition during a liquid phase of preparation of the composition.

Example 24 is a method of manufacturing a composition. The method includes mixing a composition comprising palm kernel oil and plant based aloe vera extract, wherein the palm kernel oil and the plant based aloe vera extra are present in a 1:1 ratio. The method includes sealing the composition in a sealed container when the palm kernel oil and the aloe vera plant extract are in liquid form. The method includes resting the composition in the sealed container in a refrigerated environment until a portion of the palm kernel oil transitions to a solid form. The method includes agitating the composition in the sealed container until the composition transitions to a solid form.

According to one or more embodiments of the disclosure, a composition may include a combination of all or some, but not all, of the following ingredients:
 (a) palm kernel oil;
 (b) aloe vera plant extract from inner fillet;
 (c) aloe vera plant extract from whole leaf;
 (d) phosphoric acid;
 (e) sodium benzoate;
 (f) white vinegar;
 (g) apple cider vinegar;
 (h) coconut vinegar;
 (i) wine vinegar;
 (j) rice vinegar;
 (k) malt vinegar;
 (l) lavender essential oil;
 (m) peppermint essential oil;
 (n) lemon essential oil;
 (o) rosemary essential oil; and/or
 (p) other suitable essential oils.

With respect to ingredient (a) note above, for example, the amount of palm kernel oil that may be included in the final composition is based on a percent by weight of the total weight of the final composition described herein. The composition may include ingredient (a), for example, in concentrations as follows:
 (a1) from 40% to 70% by weight the total composition;
 (a2) from 45% to 65% by weight the total composition;
 (a3) from 40% to 60% by weight the total composition;
 (a4) from 41% to 60% by weight the total composition;
 (a5) from 42% to 60% by weight the total composition;
 (a6) from 43% to 60% by weight the total composition;
 (a7) from 44% to 60% by weight the total composition;
 (a8) from 45% to 60% by weight the total composition;
 (a9) from 46% to 60% by weight the total composition;
 (a10) from 47% to 60% by weight the total composition;
 (a11) from 48% to 60% by weight the total composition;
 (a12) from 49% to 60% by weight the total composition;
 (a13) from 50% to 60% by weight the total composition;
 (a14) from 40% to 59% by weight the total composition;
 (a15) from 40% to 58% by weight the total composition;
 (a16) from 40% to 57% by weight the total composition;
 (a17) from 40% to 56% by weight the total composition;
 (a18) from 40% to 55% by weight the total composition;
 (a19) from 40% to 54% by weight the total composition;
 (a20) from 40% to 53% by weight the total composition;
 (a21) from 40% to 52% by weight the total composition;
 (a22) from 40% to 51% by weight the total composition;
 (a23) from 40% to 50% by weight the total composition;
 (a24) from 48% to 52% by weight the total composition;
 (a25) from 49% to 51% by weight the total composition.

With respect to ingredient (b) note above, for example, the amount of aloe vera plant extract from the inner fillet that may be included in the final composition is based on a percent by weight of the total weight of the final composition described herein. The composition may include ingredient (b), for example, in concentrations as follows:
 (b1) from 40% to 70% by weight the total composition;
 (b2) from 45% to 65% by weight the total composition;
 (b3) from 40% to 60% by weight the total composition;
 (b4) from 41% to 60% by weight the total composition;
 (b5) from 42% to 60% by weight the total composition;
 (b6) from 43% to 60% by weight the total composition;
 (b7) from 44% to 60% by weight the total composition;
 (b8) from 45% to 60% by weight the total composition;
 (b9) from 46% to 60% by weight the total composition;
 (b10) from 47% to 60% by weight the total composition;
 (b11) from 48% to 60% by weight the total composition;
 (b12) from 49% to 60% by weight the total composition;
 (b13) from 50% to 60% by weight the total composition;
 (b14) from 40% to 59% by weight the total composition;
 (b15) from 40% to 58% by weight the total composition;
 (b16) from 40% to 57% by weight the total composition;
 (b17) from 40% to 56% by weight the total composition;
 (b18) from 40% to 55% by weight the total composition;
 (b19) from 40% to 54% by weight the total composition;
 (b20) from 40% to 53% by weight the total composition;
 (b21) from 40% to 52% by weight the total composition;
 (b22) from 40% to 51% by weight the total composition;
 (b23) from 40% to 50% by weight the total composition;
 (b24) from 48% to 52% by weight the total composition;
 (b25) from 49% to 51% by weight the total composition;
 (b26) from 20% to 35% by weight the total composition;
 (b27) from 20% to 33% by weight the total composition;
 (b28) from 20% to 30% by weight the total composition;
 (b29) from 23% to 30% by weight the total composition;
 (b30) from 25% to 30% by weight the total composition;
 (b31) from 5% to 25% by weight the total composition;
 (b32) from 5% to 30% by weight the total composition.

With respect to ingredient (c) note above, for example, the amount of aloe vera plant extract from the whole leaf that may be included in the final composition is based on a percent by weight of the total weight of the final composition described herein. The composition may include ingredient (c), for example, in concentrations as follows:
 (c1) from 40% to 70% by weight the total composition;
 (c2) from 45% to 65% by weight the total composition;
 (c3) from 40% to 60% by weight the total composition;
 (c4) from 41% to 60% by weight the total composition;
 (c5) from 42% to 60% by weight the total composition;
 (c6) from 43% to 60% by weight the total composition;
 (c7) from 44% to 60% by weight the total composition;
 (c8) from 45% to 60% by weight the total composition;
 (c9) from 46% to 60% by weight the total composition;
 (c10) from 47% to 60% by weight the total composition;
 (c11) from 48% to 60% by weight the total composition;
 (c12) from 49% to 60% by weight the total composition;
 (c13) from 50% to 60% by weight the total composition;
 (c14) from 40% to 59% by weight the total composition;
 (c15) from 40% to 58% by weight the total composition;
 (c16) from 40% to 57% by weight the total composition;
 (c17) from 40% to 56% by weight the total composition;

(c18) from 40% to 55% by weight the total composition;
(c19) from 40% to 54% by weight the total composition;
(c20) from 40% to 53% by weight the total composition;
(c21) from 40% to 52% by weight the total composition;
(c22) from 40% to 51% by weight the total composition;
(c23) from 40% to 50% by weight the total composition;
(c24) from 48% to 52% by weight the total composition;
(c25) from 49% to 51% by weight the total composition;
(c26) from 20% to 35% by weight the total composition;
(c27) from 20% to 33% by weight the total composition;
(c28) from 20% to 30% by weight the total composition;
(c29) from 23% to 30% by weight the total composition;
(c30) from 25% to 30% by weight the total composition;
(c31) from 5% to 25% by weight the total composition;
(c32) from 5% to 30% by weight the total composition.

The foregoing percentages, concentrations, and ratios are presented by example only and are not intended to be exhaustive or to limit the disclosure to the precise percentages, concentrations, and ratios disclosed. It should be appreciated that each value that falls within a disclosed range is disclosed as if it were individually disclosed as set forth herein. For example, a range indicating a weight percent from about 8% to about 14% additionally includes ranges beginning or ending with all values within that range, including for example a range beginning at 8.1%, 8.2%, 8.3%, and so forth.

Also, according to one or more non-limiting embodiments of the disclosure, any of the concentrations for ingredients (a) or (c), for example, as listed above, may indicate the concentration for ingredient (b) as listed above. For example, an embodiment of the disclosure may comprise, for example, (a24) from 48% to 52% by weight the total composition of palm kernel oil, and equal parts by weight aloe vera plant extract from the inner fillet and aloe vera plant extract from the whole leaf. For example, the composition may comprise all, or any combination of but not all, of the ingredients (a) thru (c).

The following are exemplary embodiments of the disclosure.

In an embodiment, a composition of the present disclosure is prepared according to the following embodiment. Using a sealable container that is large enough to allow room for agitation, such as 1.1 to 2 times larger than the volume of the ingredients including palm kernel oil and aloe vera plant extract. A container suitable and sized for retail sale is best so finished product is never opened prior to sale. A transparent container allows visual process inspection and process control. When preparing the composition, place container on a reliable scale and take its weight. Place a 1:1 ratio (±15%) of aloe vera juice and liquid (about 76° F.) palm kernel oil in the container. Aloe vera juice generally contains less than 2% phosphoric acid or citric acid (organic juice) and some small quantity (1/10 of 1%) benzoate of soda. The palm kernel oil may be extracted using one or more different methods of extraction. In an embodiment, the palm kernel oil is a liquid when the palm kernel oil and the aloe vera plant extract are first introduced prior to agitation. Various additives including vinegars and essential oils may be added to the oil and particularly during the liquid phase. The temperature of the composition may be measured using an infrared thermometer for determining temperatures accurately and efficiently.

In an exemplary embodiment, the composition is agitated by hand in a refrigerated environment. The composition may be placed on a cold surface in a refrigerated environment while a temperature of the composition is monitored. As the composition begins to transition to a solid state, or shortly prior to the composition beginning to transition to a solid state, the composition may be inspected to observe whether the palm kernel oil is being cooled on a bottom of the container where the container contacts the cold surface. The container holding the composition may be moved and adjusted to observe whether the palm kernel oil is beginning to solidify. When the palm kernel oil begins to solidify, the composition may be vigorously agitated within the container. The composition may be vigorously agitated by hand within the container until the composition begins to solidify and thicken. This may typically take between 30 to 60 seconds of vigorous agitation depending on an initial temperature of the composition and the temperature of the refrigerated environment. Agitation of the composition may be rapidly slowed or discontinued when the composition has solidified and thickened sufficiently. The composition may then rest undisturbed until the composition has fully solidified.

In an exemplary embodiment, the composition is agitated by machine, such as a pneumatic paint shaker or other agitation advice. The composition may be agitated in a refrigerated environment, such as near an air condition unit or other refrigeration device. A sealed container housing the composition, including the liquid palm kernel oil and the liquid aloe vera plant extract, may be secured to a mechanical agitation device and agitated while the temperature of the composition is monitored. The mechanical agitation may be initiated before or shortly after the palm kernel oil begins to solidify. The mechanical agitation may be continued for a threshold amount of time, until the composition reaches a threshold temperature, or until it is visually observed that the composition has solidified and thickened to a sufficient degree. The solidification of the composition may be observed with a bright light while the composition is agitated.

In an embodiment, a prepared composition as disclosed herein may maintain freshness for six months or more when refrigerated in a sealed container. The freshness of the composition may deteriorate a quicker speed when the sealed container is opened.

The foregoing description has been presented for the purposes of illustration and description. It is not intended to be exhaustive or to limit the disclosure to the precise form disclosed. Many modifications and variations are possible in light of the above teaching. Further, it should be noted that alternate implementations may be used in any combination desired to form additional hybrid implementations of the disclosure.

The foregoing description has been presented for the purposes of illustration and description. It is not intended to be exhaustive or to limit the disclosure to the precise form disclosed. Many modifications and variations are possible in light of the above teaching. Further, it should be noted that any or all the aforementioned alternate implementations might be used in any combination desired to form additional hybrid implementations of the disclosure.

Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications, and their equivalents.

What is claimed is:
1. A composition comprising:
  palm kernel oil; and
  aloe vera plant extract;

wherein the palm kernel oil comprises from about 40% to about 60% by weight of the total composition; and wherein the aloe vera plant extract comprises from about 40% to about 60% by weight of the total composition.

2. The composition of claim 1, wherein the palm kernel oil and the aloe vera extract are warmed to generate a liquid mixture comprising liquid palm kernel oil and liquid aloe vera plant extract, and wherein the liquid mixture is sealed in a container in liquid form, and wherein the liquid mixture is chilled until a portion of the composition transitions to a solid state to form a partially solid mixture, and wherein the partially solid mixture is agitated until the partially solid mixture transitions to a fully solid state comprising the palm kernel oil in a solid state and the aloe vera plant extract in a solid state.

3. The composition of claim 1, wherein the palm kernel oil and the aloe vera plant extract are present in a 1:1 ratio.

4. The composition of claim 1, wherein the aloe vera plant extract comprises one or more of:

aloe vera plant extract from an inner fillet of an aloe vera plant; or aloe vera plant extract from a whole leaf of an aloe vera plant.

5. The composition of claim 1, wherein the palm kernel oil is extracted by way of one or more of:

a mechanical process; or a wet process using solvents;

wherein the palm kernel oil is not refined, bleached, or deodorized.

6. The composition of claim 1, wherein the palm kernel oil is partially hydrogenated.

7. The composition of claim 1, wherein preparation of the composition comprises:

sealing the composition in a sealed container when the palm kernel oil and the aloe vera plant extract are in liquid form;

resting the composition in the sealed container in a refrigerated environment until a portion of the palm kernel oil transitions to a solid form; and agitating the composition in the sealed container until the composition transitions to a solid form.

8. The composition of claim 1, wherein the composition comprises an emulsion that is stable in a solid form at a temperature below 25° Celsius.

9. The composition of claim 1, further comprising one or more of an essential oil or a vinegar.

10. The composition of claim 1, further comprising one or more of phosphoric acid or sodium benzoate.

11. The composition of claim 1, further comprising an effective amount of one or more preservatives.

12. The composition of claim 1, wherein the composition is prepared for topical application.

* * * * *